United States Patent
Gruber et al.

(10) Patent No.: US 7,717,637 B2
(45) Date of Patent: May 18, 2010

(54) APPLIANCE, CARTRIDGE AND SYSTEM FOR PERSONAL CARE WITH AUXILIARY FLUID

(75) Inventors: Paul Gruber, Bodensdorf (AT); Peter Haefele, Unterbergen (AT); Christian Mikula, Wernberg (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 1026 days.

(21) Appl. No.: 10/562,871

(22) PCT Filed: Jun. 24, 2004

(86) PCT No.: PCT/IB2004/050993

§ 371 (c)(1),
(2), (4) Date: Dec. 29, 2005

(87) PCT Pub. No.: WO2005/000541

PCT Pub. Date: Jan. 6, 2005

(65) Prior Publication Data

US 2006/0150419 A1    Jul. 13, 2006

(30) Foreign Application Priority Data

Jun. 30, 2003  (EP) .................................. 03101948

(51) Int. Cl.
*A46B 11/04* (2006.01)
*A47L 13/22* (2006.01)
(52) U.S. Cl. ..................................................... 401/270
(58) Field of Classification Search ................. 401/270, 401/271, 272, 275, 280, 292, 263, 132
See application file for complete search history.

(56) References Cited

U.S. PATENT DOCUMENTS 3,217,720 A    11/1965    Cyzer (Continued)

FOREIGN PATENT DOCUMENTS

CH                653595    A5    1/1986

(Continued)

*Primary Examiner*—Huyen Le

(57) ABSTRACT

The invention relates to an appliance for personal care (3) comprising a fluid channel (4) having an inlet opening (5) and an outlet opening (6), a coupling structure (7) for coupling an outlet opening (18) of a cartridge (8) for storing an auxiliary fluid to the inlet opening (5) of the fluid channel (4), said coupling structure (7) comprising a contact element (71) with at least one orifice (75) forming the inlet opening (5) of the fluid channel (4), which contact element (71) is connectable to the outlet opening (18) of the cartridge (8), and a sealing element (72) which is moveable relative to the contact element (71) between a first position in which it covers the orifice (75) and a second position in which it is released from said orifice (75), said sealing element (72) comprising engagement means (73) for engaging with means (83) in the cartridge and moving the sealing element (72) to the first position upon disconnection of the cartridge (8) from the appliance (3). The invention furthermore relates to a cartridge (8) for use with an appliance for personal care (3), said cartridge comprising a space for storage of an auxiliary fluid and an outlet opening for coupling the cartridge to said appliance, wherein the cartridge comprises means (83) for cooperating with the engagement means (73) of the sealing element (72) of the coupling structure (7), and to a system comprising such an appliance and such a cartridge.

12 Claims, 4 Drawing Sheets

U.S. PATENT DOCUMENTS

Figure 1:
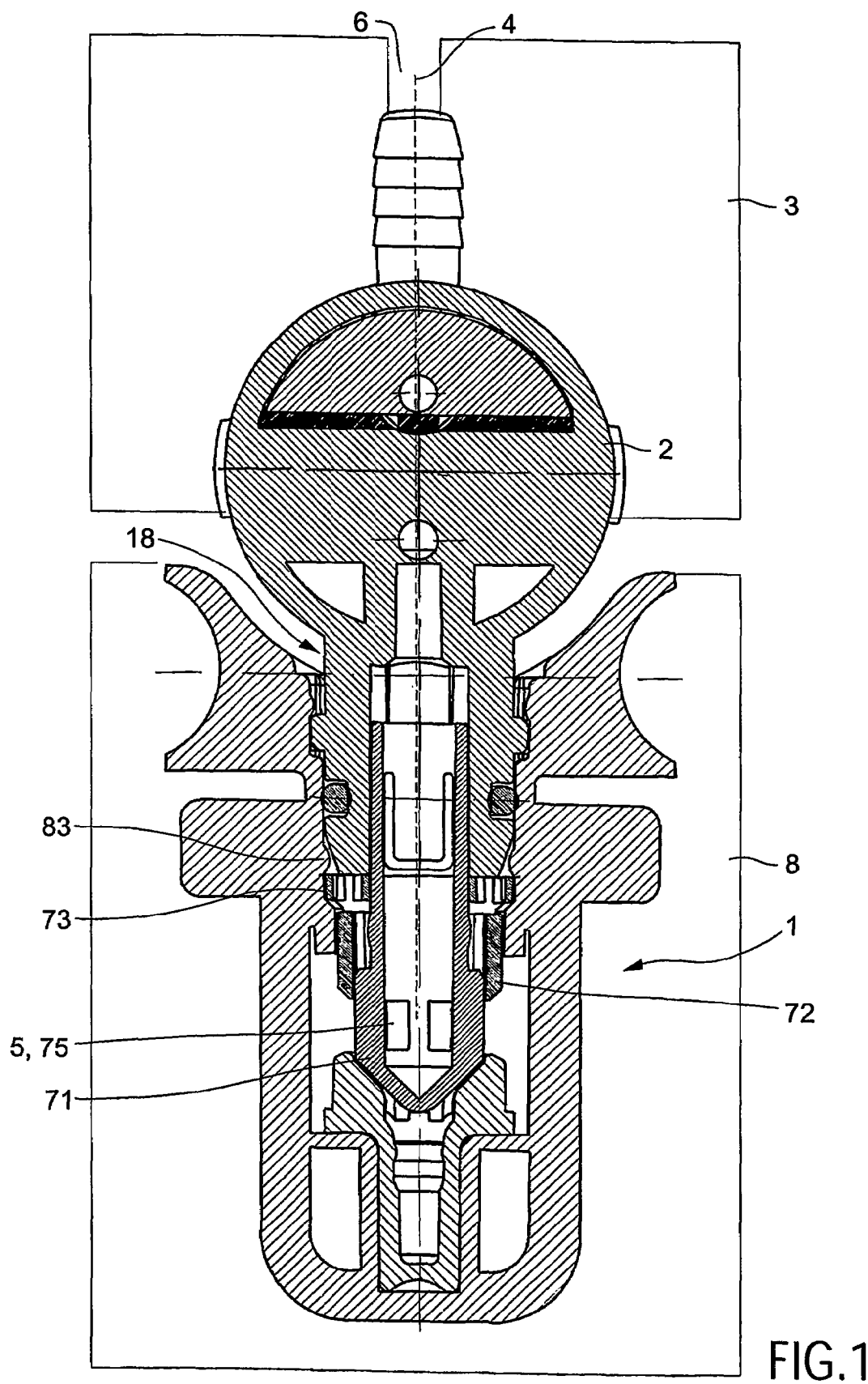

| | | | |
|---|---|---|---|
| 4,375,864 A | 3/1983 | Savage | |
| 5,134,775 A | 8/1992 | Althaus et al. | |
| 5,738,144 A | 4/1998 | Rogers | |
| 6,039,301 A | 3/2000 | Westerhof | |
| 6,363,948 B2* | 4/2002 | Choi | 132/313 |
| 7,314,329 B1* | 1/2008 | Byun | 401/279 |
| 7,357,587 B2* | 4/2008 | D'Angelo | 401/25 |
| 2002/0029478 A1 | 3/2002 | Haws et al. | |
| 2002/0032964 A1 | 3/2002 | Westerhof et al. | |
| 2003/0116197 A1 | 6/2003 | Taylor | |

FOREIGN PATENT DOCUMENTS

| | | |
|---|---|---|
| WO | WO 98/55274 | 12/1998 |
| WO | 2002/041802 A1 | 5/2002 |

* cited by examiner

APPLIANCE, CARTRIDGE AND SYSTEM FOR PERSONAL CARE WITH AUXILIARY FLUID

The invention relates to an appliance for personal care comprising a fluid channel having an inlet opening and an outlet opening, and a coupling structure for coupling an outlet opening of a cartridge for storing an auxiliary fluid to the inlet opening of the fluid channel.

The invention further relates to a cartridge for use with an appliance for personal care comprising a fluid channel having an inlet opening and an outlet opening, and a coupling structure for coupling an outlet opening of said cartridge to the inlet opening of the fluid channel, said cartridge comprising a space for storage of an auxiliary fluid and said outlet opening for coupling the cartridge to said appliance.

The invention further relates to a system for personal care comprising such an appliance for personal care and such a cartridge.

An appliance, a cartridge, and a system for personal care of the type described in the opening paragraph are known from WO 98/55274. The known system comprises a shaver provided with a cartridge comprising a space for holding an auxiliary fluid. The outlet opening of the cartridge can be coupled to the inlet opening of the fluid channel of the appliance. During operation, fluid is transported from the cartridge via the fluid channel towards a shaving head and thus to the contact area between the shaving head and the skin of a user. The fluid cartridge is a disposable cartridge which can be replaced with a new filled cartridge after use.

A disadvantage of the known appliance is that the inlet opening of the fluid channel is left open when the cartridge is disconnected from the appliance. After use the fluid channel will contain some residual fluid, which may drip out of the fluid channel and the inlet opening after removal of the cartridge. Furthermore, the fluid channel is susceptible to contamination, and after some time the remaining fluid will dry and clog up the fluid channel, thus hampering the fluid transport in the appliance.

It is an object of the invention to provide an improved appliance for personal care which is hygienic in use and for which a proper fluid application function is ensured. To achieve this object, an appliance for personal care according to the invention is characterized in that said coupling structure comprises a contact element with at least one orifice forming the inlet opening of the fluid channel, which contact element is connectable to the outlet opening of the cartridge, and a sealing element which is movable relative to the contact element between a first position in which it covers the orifice and a second position in which it is released from said orifice, said sealing element comprising engagement means for engaging with means in the cartridge and moving the sealing element into the first position upon disconnection of the cartridge from the appliance.

When the outlet opening of a cartridge is connected to the coupling structure, the sealing element is in the second position and released from the orifice in the contact element. Thus the inlet opening of the fluid channel is open and ready for the passage of fluid coming from the cartridge during operation. Upon disconnection of the cartridge from the appliance, the engagement means comprised in the sealing element engage with means in the cartridge and take along the sealing element into the first position, in which it covers the orifice in the contact element and thus the inlet opening of the fluid channel. In this manner the inlet opening of the fluid channel is sealed against contamination from the outside, and clogging of remaining fluid in the fluid channel is prevented.

An embodiment of an appliance for personal care according to the invention is characterized in that said engagement means for engaging with means in the cartridge are arranged for moving the sealing element into the second position upon connection of the cartridge to the appliance. The action of connecting the cartridge to the appliance causes the engagement means comprised in the sealing element to engage with means in the cartridge and to take along the sealing element to the second position, in which it released from the orifice in the contact element.

It is advantageous when the sealing element is releasably blocked in the first position. In this manner the sealing element maintains its first position covering the inlet opening of the fluid channel and is not susceptible to an unwanted release of the orifice upon a movement of the appliance.

An embodiment of an appliance for personal care according to the invention is characterized in that the sealing element comprises an annular body which is slidable along an outside surface of the contact element, said engagement means comprising a collar for cooperation with protuberances in the outlet opening of the cartridge.

A further embodiment of an appliance for personal care according to the invention is characterized in that the sealing element comprises a plug which is slidable along an inner surface of the contact element, said engagement means comprising a cavity in said plug for receiving a protruding end portion provided in the outlet opening of the cartridge.

It is advantageous when the contact element comprises a longitudinally extending part provided with a tapered end. The outlet opening of a new, unused cartridge may comprise a seal made of foil or the like. The tapered end of the contact element can pierce this seal upon connection to the cartridge and the coupling structure so as to open the outlet opening of the cartridge.

The invention also relates to a cartridge for use with an appliance for personal care comprising a fluid channel having an inlet opening and an outlet opening, a coupling structure for coupling an outlet opening of said cartridge to the inlet opening of the fluid channel, said coupling structure comprising a contact element with at least one orifice forming the inlet opening of the fluid channel, which contact element is connectable to the outlet opening of the cartridge, and a sealing element which is movable relative to the contact element between a first position in which it covers the orifice and a second position in which it is released from said orifice, said sealing element comprising engagement means for engaging with means in the cartridge and moving the sealing element into the first position upon disconnection of the cartridge from the appliance, said cartridge comprising a space for storage of an auxiliary fluid and said outlet opening for coupling the cartridge to said appliance, characterized in that the cartridge comprises means for cooperating with the engagement means of the sealing element of the coupling structure.

An embodiment of a cartridge according to the invention is characterized in that said means comprise protuberances for engagement with a collar of an annular body which is slidable along an outer surface of the contact element.

A further embodiment of a cartridge according to the invention is characterized in that said means comprise a protruding end portion for engagement with a cavity in a slidable plug provided in the contact element.

An embodiment of a cartridge according to the invention is characterized in that its outlet opening is provided with a closing member which is movable from the outlet opening upon coupling of the contact element of the coupling structure to the cartridge.

The invention further relates to a system for personal care comprising a cartridge having a space for storing an auxiliary fluid and an appliance according to the invention.

Figure 2A:
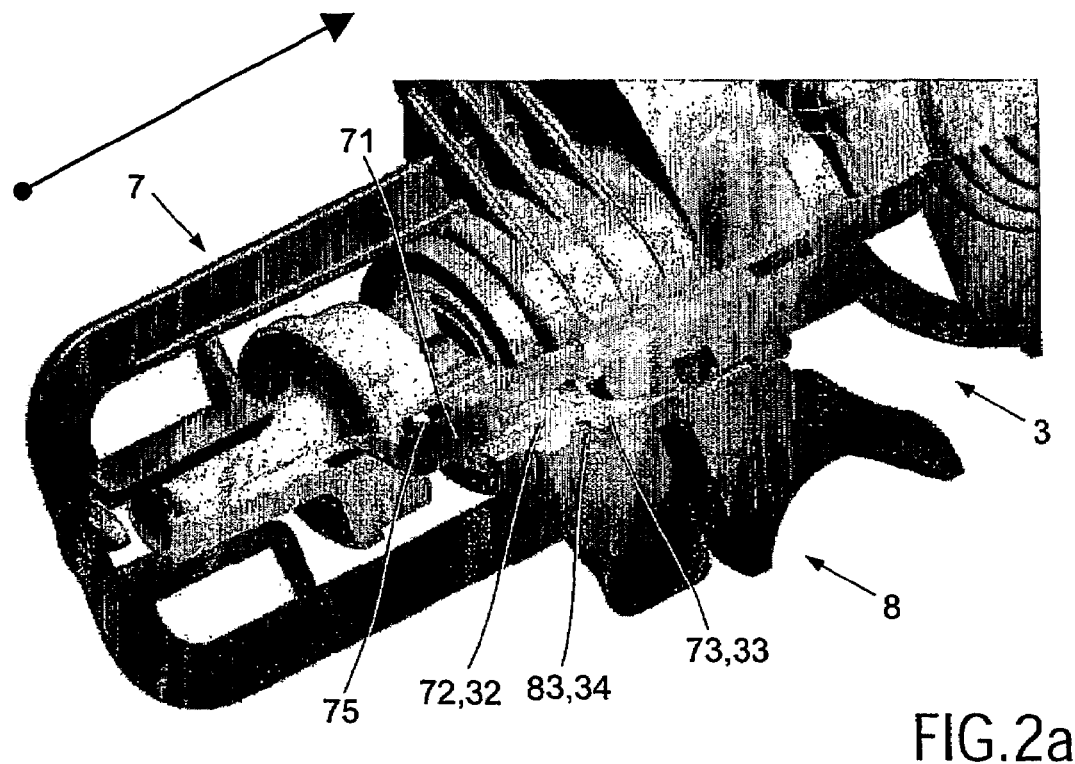
Figure 2B:
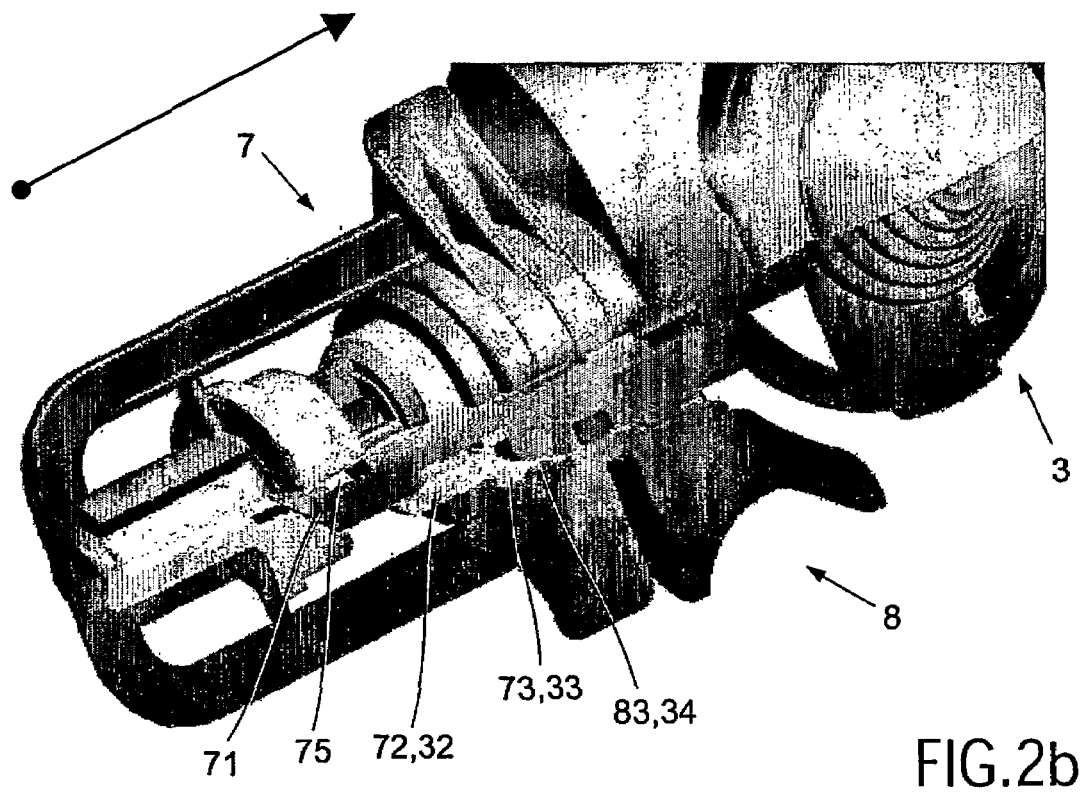
Figure 3A:
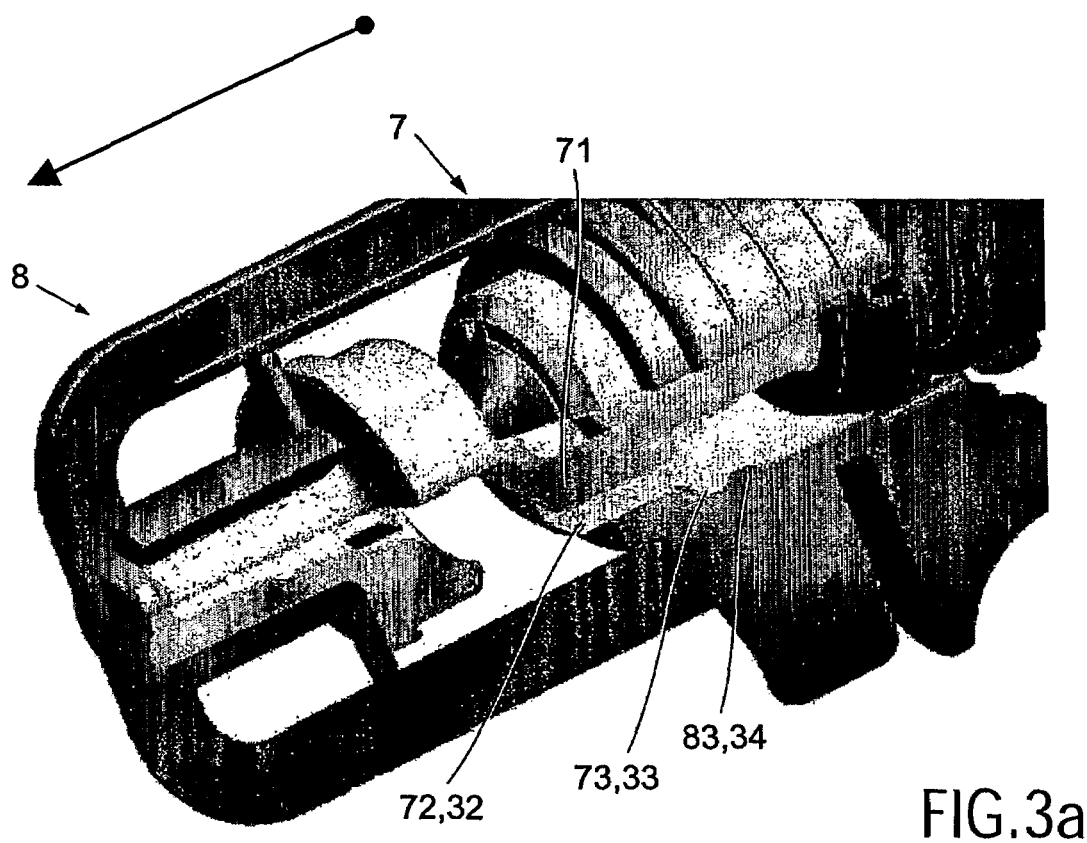
Figure 3B:
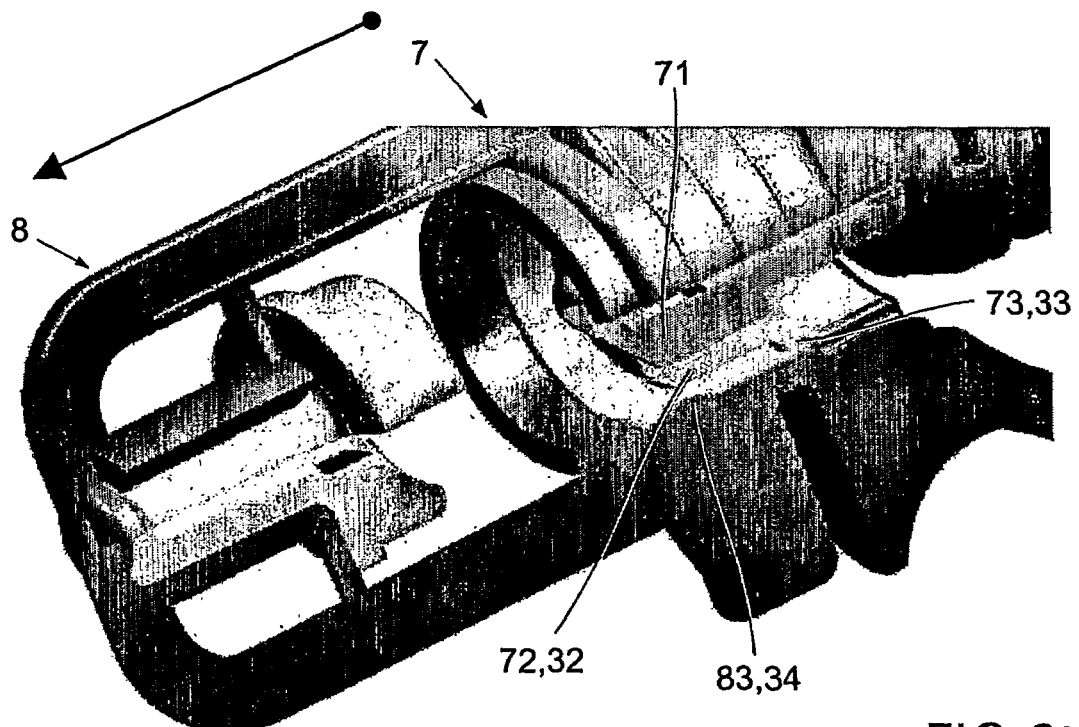
Figure 4A:
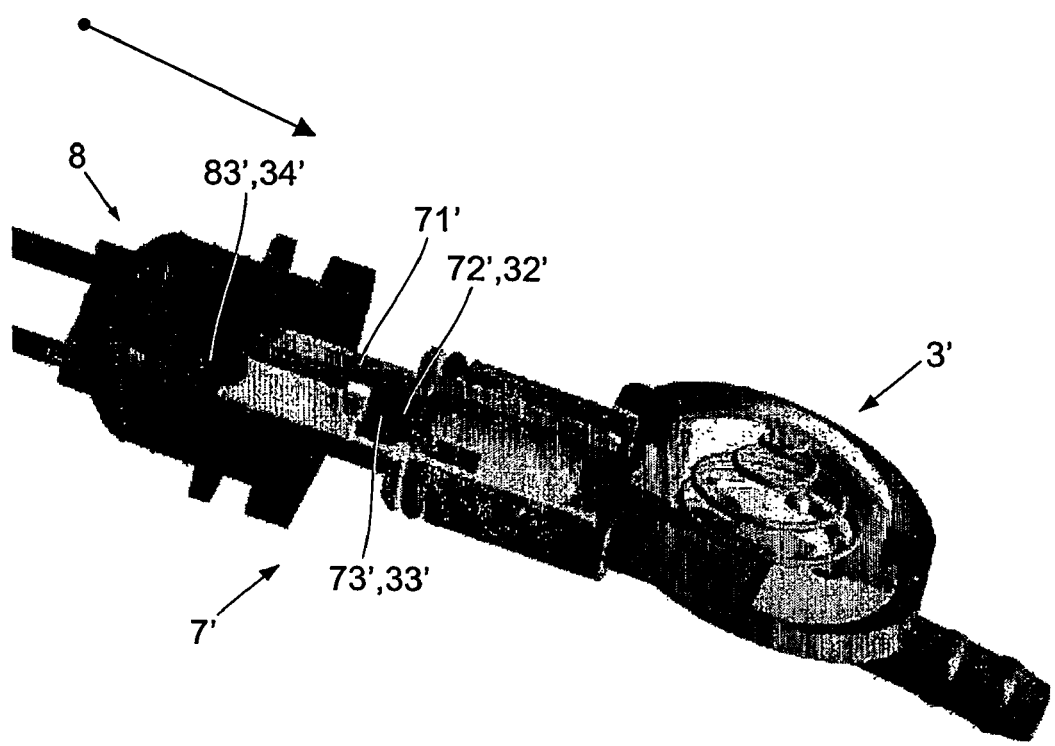
Figure 4B:
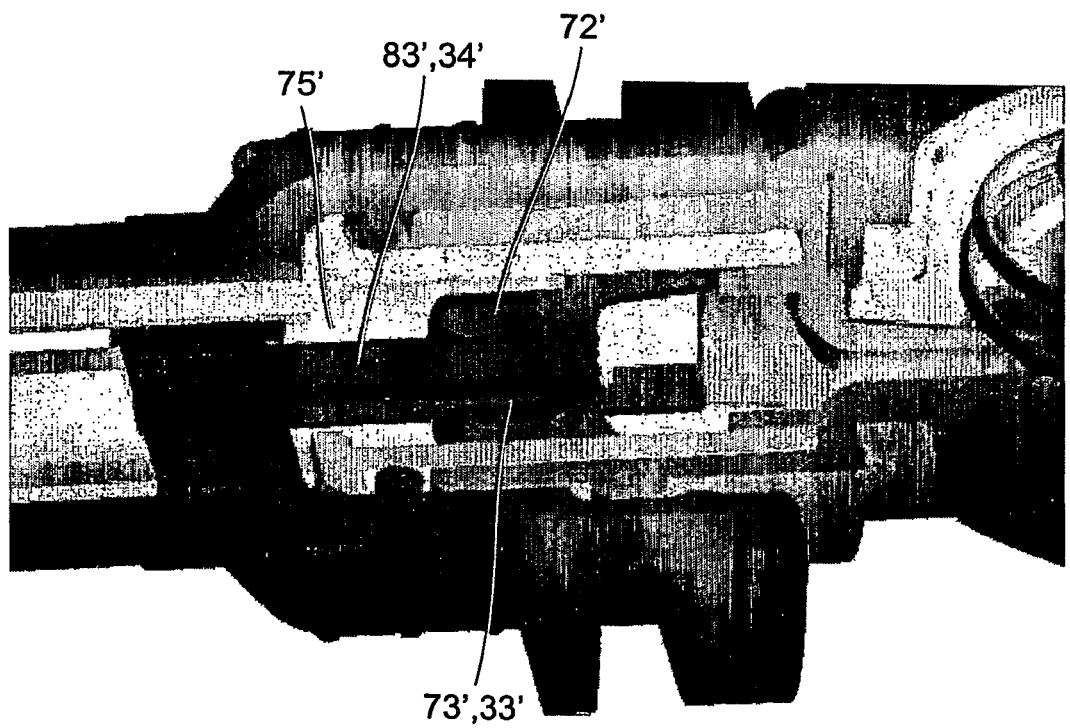

The invention will be described in more detail hereinafter with reference to the drawings, in which FIG. 1 schematically shows a first embodiment of a coupling structure and a cartridge according to the invention, FIGS. 2*a* and 2*b* show a detail of the coupling structure and the cartridge of FIG. 1 during connection, FIGS. 3*a* and 3*b* show a detail of the coupling structure and the cartridge of FIG. 1 during disconnection, FIGS. 4*a* and 4*b* show a further embodiment of a coupling structure and a cartridge according to the invention.

FIG. 1 shows a first embodiment of a coupling structure 7 and a cartridge 8 according to the invention. In this embodiment said coupling structure 7 is comprised in an appliance for personal care, schematically indicated by 3 in FIG. 1. The appliance 3 comprises a fluid channel 4, indicated with a broken line, having an inlet opening 5 and an outlet opening 6, and a coupling structure 7 for coupling an outlet opening 18 of the cartridge 8 for storing an auxiliary fluid to the inlet opening 5 of the fluid channel 4. This appliance for personal care may comprise, for example, an electric toothbrush, in which auxiliary fluid is transported from the cartridge 8 via the coupling structure 7 to the outlet opening 6 located between the bristles of the toothbrush. The fluid is delivered via the bristles to the teeth when the bristles are brought into contact with the teeth. It is noted that the appliance for personal care may also comprise any other type of appliance for personal care in which an auxiliary fluid is applied during operation such as, for example, a shaver, a depilation device, a massaging device, a facial treatment device, etc. The auxiliary fluid to be used with the appliance is chosen in dependence on the type of appliance for personal care, for example liquid toothpaste for a toothbrush, a shaving fluid for a shaver, or a cleansing gel for a facial treatment device.

The cartridge may comprise, for example, a cartridge with a space formed by a flexible foil bag for holding an auxiliary fluid. However, it may alternatively comprise a cartridge made from a different material. In this embodiment, the fluid channel 4 is furthermore provided with an electrically activated pump unit 2 to transport fluid from the cartridge 8 via the fluid channel 4 towards the outlet opening 6. It is noted that fluid transport may also be realised in other ways, such as manual pumping, or by means of vibrations in the appliance that draw fluid out of the cartridge through the fluid channel to the outlet opening.

The coupling structure 7 comprises a contact element 71 with at least one orifice 75 forming the inlet opening 5 of the fluid channel 4, which contact element is connectable to the outlet opening 18 of the cartridge, and a sealing element 72 which is movable relative to the contact element 71 between a first position in which it covers the orifice 75 and a second position in which it is released from said orifice 75, said sealing element 72 comprising engagement means 73 for engaging with means 83 in the cartridge 8 and moving the sealing element 72 into the first position upon disconnection of the cartridge 8 from the appliance 3. This will be further elucidated in FIGS. 2 and 3.

As can be seen in FIG. 1, the contact element 71 comprises a longitudinally extending part provided with a tapered end. The outlet opening of the cartridge may be provided with a closing member which is movable from the outlet opening upon coupling of the contact element of the coupling structure to the cartridge, in this embodiment a seal made of foil or the like covering the outlet opening 18 of the cartridge. The tapered end of the contact element can pierce this seal upon connection to the cartridge and the coupling structure so as to open the outlet opening of the cartridge. In FIG. 1, the sealing element 72 is shown in the second position, in which the sealing element 72 is released from the orifice 75. In this manner an open fluid path is created between the cartridge 8 and the fluid channel 4, and the appliance is ready for operation. The sealing element in this embodiment 72 comprises an annular body 32 which is slidable along an outer surface of the contact element 71, and said engagement means 73 comprise a collar 33 for cooperation with protuberances 34 in the outlet opening 18 of the cartridge 8.

FIG. 2*a* shows a detail of the coupling structure 7 and the cartridge 8 during connection. In the following Figures, only the part of the cartridge that is in contact with the coupling structure is shown for clarity. It is furthermore noted that in the following description, the cartridge is moved relative to the coupling structure which is in a stationary position; it is to be understood that this movement of the cartridge relative to the stationary coupling structure in the direction of the arrows, is similar to a movement of the coupling structure relative to a stationary cartridge in a direction opposite to the direction of these arrows.

Before the contact element 71 and the cartridge 8 are connected, the sealing element 72 is in the first position covering the orifice 75, thus sealing off the inlet opening of the fluid channel 4. The sealing element is releasably blocked in this first position, so that it is not susceptible to an unwanted release of the orifice upon a movement of the appliance.

The contact element 71 with the sealing element 72 is inserted into the outlet opening 18 of the cartridge 8, and the cartridge 8 is moved in the direction of the arrow. Upon connection, the collar 33 of the annular body 32 engages with the protuberances 34 of the cartridge, and the annular body is moved away from the orifice 75 in the direction of the arrow. Upon a further movement of the cartridge 8 in the direction of the arrow, the protuberances 34 slide over the collar 33 and the annular body 32 is in the second position, in which it is released from the orifice 75, as can be seen in FIG. 2*b*. A fluid path is thus created from the space in the cartridge storing the auxiliary fluid via the orifice 75 and the fluid path 4 through the appliance 3 (not shown here). Activation of the pump unit causes the auxiliary fluid to be transported from the cartridge via the orifice 75 and the fluid channel 4 towards the application area of the appliance, the bristles in the case of a toothbrush.

After operation of the appliance, the cartridge is emptied and needs to be disconnected from the appliance and replaced with a new filled cartridge. This may be after one operation, or after a number of operations. Depending on the chosen appliance and fluid, the cartridge may comprise an amount of fluid for only one use, or for a number of uses. FIG. 3*a* shows a detail of the coupling structure 7 and the cartridge 2 during disconnection. The cartridge 8 is moved in the direction of the arrow, and the collar 33 of the annular body 32 engages with the protuberances 34 of the cartridge 8. The annular body 32 is kept in its position and thus slides relative to the contact element towards the first position, in which it again covers the orifice 75 in the contact element 71.

Upon a further movement of the cartridge 8 in the direction of the arrow, the protuberances 34 slide over the collar 33 while the annular body 32 is in the second position, in which it covers the orifice 75, as can be seen in FIG. 3*b*. The cartridge is then completely disconnected from the coupling element 7. Since the orifice 75 is covered by the annular body 32, the inlet opening of the fluid path 4 is sealed against contamination from the outside, and clogging of remaining fluid in the fluid channel is prevented. In this manner a correct operation of the fluid transport in the appliance is ensured upon connection of a new cartridge. Furthermore, the appliance's fluid path is less susceptible to contamination, which renders the appliance more hygienic. This is especially advantageous if the user waits a relatively long time before a new cartridge is attached to the appliance.

FIGS. 4a and 4b show a further embodiment of a coupling structure 7' and a cartridge 8' according to the invention. In this embodiment, the sealing element 72' comprises a plug 32' which is slidable along an inner surface of the contact element 71', and the engagement means 73' comprise a cavity 33' in said plug for receiving a protruding end portion 34' provided in the outlet opening 18' of the cartridge 8'. Before the contact element 71' and the cartridge 8' are connected, the plug 32' is in a first position resting against a shoulder on the inner surface of the contact element 71', thus sealing off the inlet opening 75' of the fluid channel 4'.

FIG. 4a shows a detail of the coupling structure 7' and the cartridge 8' during connection. The cartridge 8' is moved in the direction of the arrow relative to the coupling structure 7'. As shown in FIG. 4b, the protruding end portion 34' engages with the cavity 33' in the plug 32', and the plug 32' is moved along the inner surface of the contact element 71' away from the inner shoulder, to release the inlet opening 75' of the fluid channel 4' and to open the fluid path between the cartridge 8' and the appliance 3'. Upon a movement of the cartridge in a direction opposite the direction of the arrow, in order to disconnect the cartridge from the coupling structure 7', the protruding end portion 34' takes along the plug 72 in this opposite direction. The plug 32' then engages with the inner shoulder and seals off the inlet opening of the fluid channel again, and the protruding end portion 34' becomes disengaged from the cavity 33' in the plug 32'.

Since the inlet opening 75' is closed by the plug 32', the inlet opening of the fluid path 4 is sealed against contamination from the outside, and clogging of remaining fluid in the fluid channel is prevented when no cartridge is connected to the appliance. In this manner a correct operation of the fluid transport in the appliance is ensured upon connection of a new cartridge. Furthermore, the appliance's fluid path is less susceptible to contamination, which renders the appliance more hygienic.

It is noted that the cartridge may be removably mounted inside the body of the appliance for personal care, for example in the handle of an electronic toothbrush. The cartridge may, however, also be located on an outside surface of the body of the appliance.

It is furthermore noted that the advantage described above of sealing off of the inlet opening of the fluid path when no cartridge is attached is achieved because the coupling structure comprises a contact element with at least one orifice forming the inlet opening of the fluid channel, which contact element is connectable to the outlet opening of the cartridge, and a sealing element which is movable relative to the contact element between a first position in which it covers the orifice and a second position in which it is released from said orifice, said sealing element comprising engagement means for engaging with means in the cartridge and moving the sealing element into the first position upon disconnection of the cartridge from the appliance.

An additional advantage is that a possible connection of unsuitable cartridges can be avoided because of the cooperation between the engagement means of the sealing element and the means in the cartridge. The use of an auxiliary fluid in conjunction with an appliance for personal care imposes special requirements on said fluid. The auxiliary fluid should be suitable for the desired treatment with the appliance, and the chemical composition of the fluid should not have a negative affect on the user nor on the appliance. It is therefore important that only cartridges with fluids have been tested and approved in conjunction with the appliance are used with the appliance. This is achieved by an appliance, a cartridge, and a system according to the invention, in which only specific cartridges with the correct means are capable of engaging with the engagement means of the sealing element of the coupling structure of the appliance so as to open and close the fluid path. In the described embodiments this is realised by a collar on the sealing element for cooperation with protuberances provided in the outlet opening of the cartridge, and a plug in the sealing element with a cavity for receiving a protruding end portion provided in the outlet opening of the cartridge. It is noted, however, that the engagement means comprised in the sealing element for engagement with means in the cartridge are not limited to the described embodiments, and may also comprise other types or combinations of means such as, for example, an annular body forming the sealing element and cooperating with snap hooks in the outlet opening of the cartridge.

The invention claimed is:

1. An appliance (3) for personal care, comprising:
   a fluid channel (4) having an inlet opening (5) and an outlet opening (6);
   a coupling structure (7) for coupling an outlet opening (18) of a cartridge (8) for storing an auxiliary fluid to the inlet opening (5) of the fluid channel (4),
   characterized in that said coupling structure (7) comprises:
   a contact element (71) with at least one orifice (75) forming the inlet opening (5) of the fluid channel (4), which contact element (71) is connectable to the outlet opening (18) of the cartridge (8), and
   a sealing element (72) which is movable relative to the contact element (71) between a first position in which it covers the orifice (75) and a second position in which it is released from said orifice (75), said sealing element (72) comprising engagement means (73) for engaging with means (83) in the cartridge and moving the sealing element (72) into the first position upon disconnection of the cartridge (8) from the appliance (3).

2. An appliance for personal care as claimed in claim 1, characterized in that said engagement means (73) for engaging with means (83) in the cartridge (8) are arranged for moving the sealing element (72) into the second position upon connection of the cartridge (8) to the appliance (3).

3. An appliance for personal care as claimed in claim 1, characterized in that the sealing element (72) is releasably blocked in the first position.

4. An appliance for personal care as claimed in claim 1, characterized in that the sealing element (72) comprises an annular body (32) which is slidable along an outer surface of the contact element (71), said engagement means (73) comprising a collar (33) for cooperation with protuberances (34) provided in the outlet opening (18) of the cartridge.

5. An appliance for personal care as claimed in claim 1, characterized in that the sealing element (72) comprises a plug (32') which is slidable along an inner surface of the contact element (71'), said engagement means (73') comprising a cavity (33') in said plug (32') for receiving a protruding end portion (34') provided in the outlet opening (18') of the cartridge (8').

6. An appliance for personal care as claimed in claim 1, characterized in that the contact element (71) comprises a longitudinally extending part provided with a tapered end.

7. An appliance for personal care as claimed in claim 1, wherein the appliance (3) is an electric toothbrush.

8. A cartridge (8) for use with an appliance for personal care (3) comprising a fluid channel (4) having an inlet opening (5) and an outlet opening (6), a coupling structure (7) for coupling an outlet opening (18) of said cartridge (8) to the inlet opening (5) of the fluid channel (4), said coupling structure (7) comprising a contact element (71) with at least one orifice (75) forming the inlet opening (5) of the fluid channel (4), which contact element (71) is connectable to the outlet opening (18) of the cartridge (8), and a sealing element (72) which is movable relative to the contact element (71) between a first position in which it covers the orifice (75) and a second position in which it is released from said orifice (75), said sealing element (72) comprising engagement means (73) for engaging with means (83) in the cartridge and moving the sealing element (72) into the first position upon disconnection of the cartridge (8) from the appliance (3), said cartridge comprising a space for storage of an auxiliary fluid and said outlet opening (18) for coupling the cartridge (8) to said appliance (3), characterized in that the cartridge (8) comprises means (83) for cooperating with the engagement means (73) of the sealing element (72) of the coupling structure (7).

9. A cartridge as claimed in claim 8, characterized in that said means (83) comprise protuberances (34) for engagement with a collar (33) of an annular body (32) which is slidable along an outer surface of the contact element (71).

10. A cartridge as claimed in claim 8, characterized in that said means (83) comprise a protruding end portion (34') for engagement with a cavity (33') in a slidable plug (32') provided in the contact element (71).

11. A cartridge as claimed in claim 8, characterized in that its outlet opening (18) is provided with a closing member which is movable out of the outlet opening (18) upon coupling of the contact element (71) of the coupling structure (7) to the cartridge (8).

12. A system for personal care, comprising a cartridge having a space for storing an auxiliary fluid as claimed in claim 8, and an appliance (3) for personal care, comprising:
 a fluid channel (4) having an inlet opening (5) and an outlet opening (6);
 a coupling structure (7) for coupling an outlet opening (18) of a cartridge (8) for storing an auxiliary fluid to the inlet opening (5) of the fluid channel (4),
 characterized in that said coupling structure (7) comprises:
 a contact element (71) with at least one orifice (75) forming the inlet opening (5) of the fluid channel (4), which contact element (71) is connectable to the outlet opening (18) of the cartridge (8), and
 a sealing element (72) which is movable relative to the contact element (71) between a first position in which it covers the orifice (75) and a second position in which it is released from said orifice (75), said sealing element (72) comprising engagement means (73) for engaging with means (83) in the cartridge and moving the sealing element (72) into the first position upon disconnection of the cartridge (8) from the appliance (3).

* * * * *